United States Patent [19]

Inukai et al.

[11] Patent Number: 5,853,371
[45] Date of Patent: Dec. 29, 1998

[54] SYSTEM AND METHOD FOR EVALUATING THE DEGREE OF ARTERIAL ELASTICITY IN A LIVING SUBJECT

[75] Inventors: Hidekatsu Inukai, Nagoya; Hiroshi Sakai, deceased, late of Komaki, both of Japan, by Hiroko Sakai, legal heir

[73] Assignee: Colin Corporation, Komaki, Japan

[21] Appl. No.: 867,978

[22] Filed: Jun. 3, 1997

[51] Int. Cl.⁶ .......................... A61B 5/0205; A61B 5/021; A61B 5/022

[52] U.S. Cl. .......................... 600/483; 600/485; 600/492; 600/504

[58] Field of Search .................... 600/483, 485, 600/492, 504

[56] References Cited

U.S. PATENT DOCUMENTS

| | | |
|---|---|---|
| 5,033,472 | 7/1991 | Sato et al. . |
| 5,309,916 | 5/1994 | Hatschek ................................. 600/485 |
| 5,379,774 | 1/1995 | Nishimura et al. ...................... 600/479 |
| 5,603,329 | 2/1997 | Hosaka et al. . |
| 5,623,933 | 4/1997 | Amano et al. . |
| 5,697,376 | 12/1997 | Nomura et al. .......................... 600/485 |
| 5,715,826 | 2/1998 | Horrocks et al. . |
| 5,724,981 | 3/1998 | Apple . |

FOREIGN PATENT DOCUMENTS 0-772-998-A2  5/1997  WIPO .

Primary Examiner—William E. Kamm
Assistant Examiner—Carl H. Layno
Attorney, Agent, or Firm—Oliff & Berridge, PLC

[57] ABSTRACT

A system and method for evaluating the degree of elasticity of a subject's arteries includes an inflatable cuff that is wrapped around a portion of the living subject. A cuff pressure regulating circuit changes the constriction pressure applied by the inflatable cuff to the subject. A time-difference determining circuit determines a time difference between predetermined periodic points on an electrocardiographic waveform of the living subject and predetermined periodic points on corresponding pressure pulse waves of the living subject. An arterial elasticity evaluation circuit determines the degree of elasticity of the subject's arteries based on the relationship between changes in the time difference determined by the time-difference determining circuit and changes in the constriction pressure applied by the inflatable cuff.

22 Claims, 9 Drawing Sheets

SYSTEM AND METHOD FOR EVALUATING THE DEGREE OF ARTERIAL ELASTICITY IN A LIVING SUBJECT

BACKGROUND OF THE INVENTION

1. Field of Invention

This invention relates to medical diagnostic systems. More specifically, this invention is directed to a device for evaluating the degree of arterial elasticity in a living subject.

2. Description of Related Art

High blood pressure is a common symptom associated with certain arterial diseases, e.g., arteriosclerosis. Although blood pressure measurement devices are effective for the measurement of a subject's blood pressure, they are ineffective in evaluating the degree of improvement of the underlying cause of the subject's high blood pressure. This is because high blood pressure patients are typically given medication to bring their blood pressure back to normal levels. Although blood pressure reducing medications treat the symptom of high blood pressure, they do not treat the underlying cause of the high blood pressure. A dietary treatment is typically used to treat the underlying cause of the high blood pressure.

Most arterial diseases result in a hardening of the subject's arteries. Thus, the progression of an arterial disease in a subject can typically be determined by the degree of arterial elasticity. However, existing blood pressure measurement devices only measure the subject's blood pressure.

SUMMARY OF THE INVENTION

This invention provides a system and method for evaluating the degree of elasticity of a subject's arteries. The system provides an inflatable cuff that is wrapped around a portion of the living subject. A cuff pressure regulating circuit changes the constriction pressure applied by the inflatable cuff to the subject. A pressure pulse wave detection circuit detects a pressure pulse wave that propagates through an artery of the subject. An electrocardiographic waveform detection circuit detects an electrocardiographic waveform that is generated by the change in electric potential of the subject's cardiac muscle. A time-difference determining circuit determines time differences between predetermined periodic points on the electrocardiographic waveform and predetermined periodic points on corresponding pressure pulse waves. An arterial elasticity evaluation circuit determines the degree of elasticity of the subject's arteries based on the relationship between changes in the time difference determined by the time-difference determining circuit and changes in the constriction pressure applied by the inflatable cuff.

These and other features and advantages of this invention are described and are apparent from the following detailed description of the preferred embodiments.

BRIEF DESCRIPTION OF THE DRAWINGS

The preferred embodiments of this invention will be described in detail, with reference to the following figures, wherein.

DETAILED DESCRIPTION OF PREFERRED EMBODIMENTS

Figure 1:
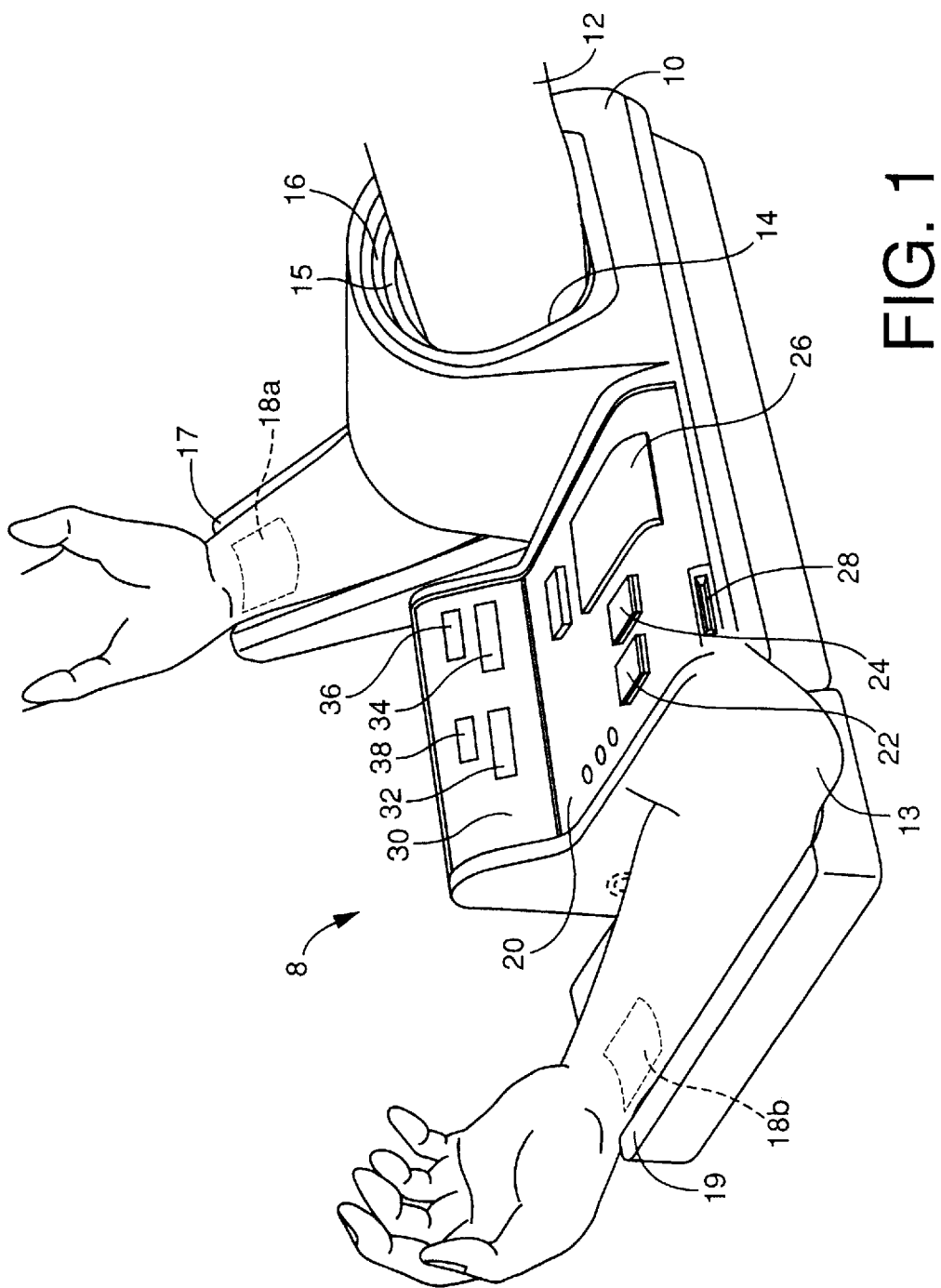
FIG. 1 is a perspective view of an automatic blood pressure measurement device incorporating the arterial elasticity evaluation system of this invention.

FIG. 1 shows an automatic blood pressure measurement device 8 that incorporates the arterial elasticity evaluation system of this invention. The device 8 comprises a housing 10 that includes an arm receptor 14 for receiving a right arm 12 of a subject for measuring the subject's blood pressure. A belt 16 is supported inside the arm receptor 14 in a generally cylindrical shape. An inflatable cuff 15, which is preferably formed by a rubber bag that is positioned inside a flexible cloth bag, is secured to the inner surface of the belt 16.

In the rear of the arm receptor 14, a first arm rest 17 is provided at a tilt to support the forearm of the subject's right arm 12. A first electrocardio electrode 18a is positioned on the arm rest 17 so that the electrocardio electrode 18a contacts the back of the forearm or hand of the subject's right arm 12 when the subject's forearm is supported by the arm rest 17. The upper surface of the arm rest 17 has a shape suitable for supporting the subject's right forearm. Thus, the muscles between the elbow and the back of the hand are maintained in a relaxed state for a more accurate detection of the subject's electrocardiographic waveform.

A second arm rest 19 is provided on the left hand side of the housing 10 for supporting the subject's left arm 13. A second electrocardio electrode 18b is positioned on an end portion of the arm rest 19. Thus, the second electrocardio electrode 18b contacts the subject's left arm 13 when the left arm 13 is supported by the second arm rest 19. The upper surface of the second arm rest 19 has a shape suitable for supporting the subject's entire left forearm. Thus, the muscles between the elbow and the back of the hand are maintained in a relaxed state for a more accurate detection of the subject's electrocardiographic waveform. The two electrocardio electrodes 18a and 18b cooperate with each other to detect the electrocardiographic waveform of the subject.

The automatic blood pressure measuring device 8 has an operation panel 20 that includes a printer 26, a card insertion slot 28, a start switch 22 and a stop switch 24. The automatic blood pressure measuring device 8 also has a display panel 30 that includes a systolic blood pressure display 32, diastolic blood pressure display 34, a heart rate display 36 and a date and time display 38.

Figure 2:
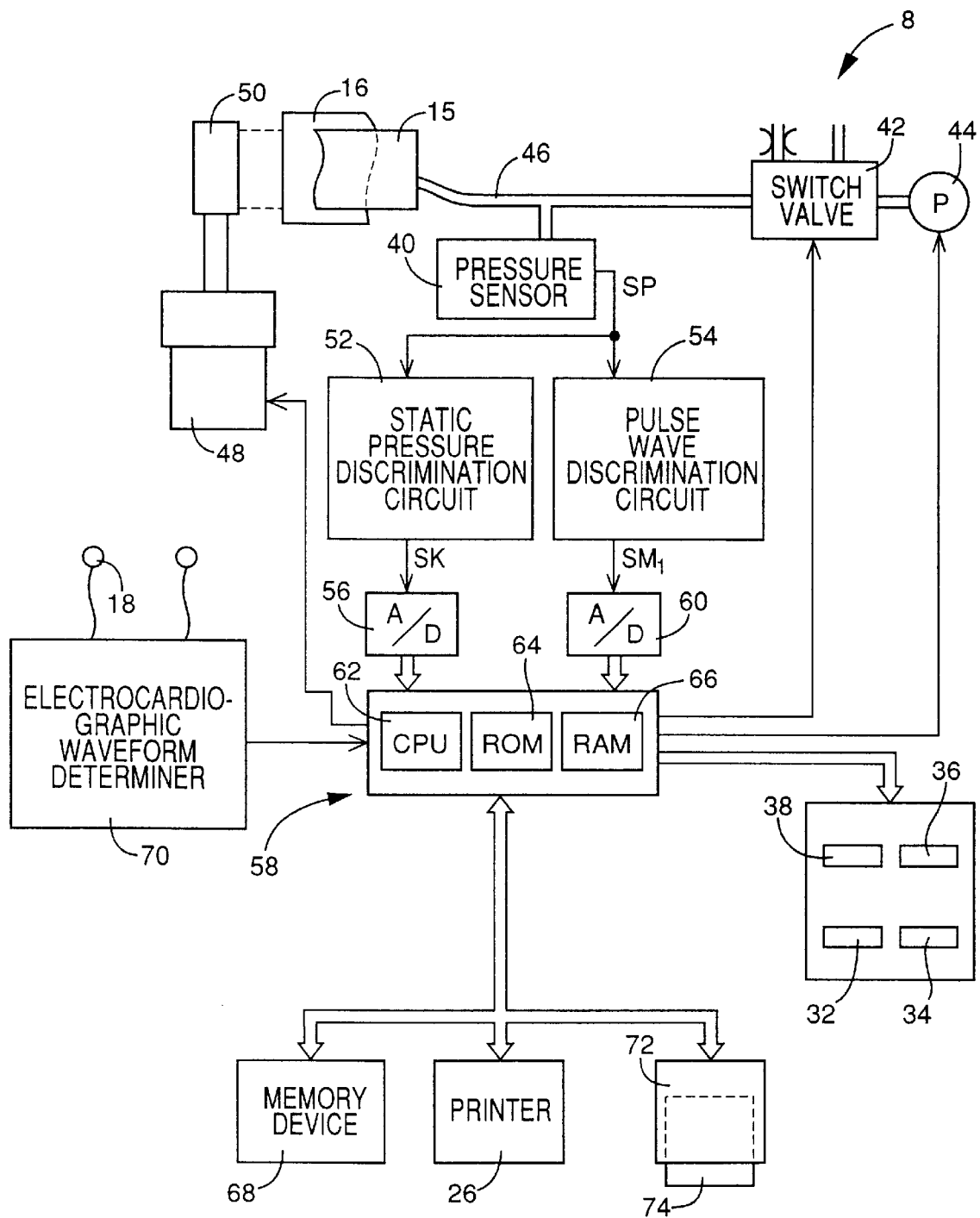
FIG. 2 is a block diagram of the automatic blood pressure measurement device of FIG. 1.

FIG. 2 shows a preferred embodiment of the arterial elasticity evaluation system of this invention.

The inflatable cuff 15 is connected via piping 46 to a pressure sensor 40, a switch valve 42 and an air pump 44.

The switch valve 42 is selectively placed in either an inflation position, a slow-deflation position or a quick-deflation position. In the inflation position, the switch valve 42 allows pressurized air from the air pump 44 to be supplied to the inflatable cuff 15. In the slow-deflation position, the switch valve 42 allows the pressurized air in the inflatable cuff 15 to be slowly discharged. In the quick-deflation position, the switch valve 42 allows the pressurized air in the inflatable cuff 15 to be quickly discharged.

The belt 16, which is supported in a cylindrical shape by the arm receptor 14 and to which the inflatable cuff 15 is secured, is attached at one of its longitudinal ends to the housing 10. The other longitudinal end of the belt 16 is attached to a rotatable drum 50 that is driven or rotated by a direct-current motor 48 via reduction gears. The belt 16/inflatable cuff 15 combination is tightened and loosened by the motor 48.

The pressure sensor 40 detects an air pressure in the inflatable cuff 15 and supplies a pressure signal SP, representing the detected pressure, to a static pressure discrimination circuit 52 and a pulse wave discrimination circuit 54. The static pressure discrimination circuit 52 includes a low-pass filter that extracts a static component contained in the pressure signal SP, i.e., a cuff pressure signal SK that represents the static cuff pressure. The cuff pressure signal SK is supplied to an electronic control device 58 via a first A/D converter 56.

The pulse wave discrimination circuit 54 includes a band-pass filter that extracts an oscillatory component of the pressure signal SP that falls within a predetermined frequency range. The oscillatory component is supplied as a cuff pulse wave signal $SM_1$ to the electronic control device 58 via a second A/D converter 60. The cuff pulse wave signal $SM_1$ represents an oscillatory pressure wave that is produced from a brachial artery of the subject and that propagates to an area on the subject's right arm 12 that is in contact with the inflatable cuff 15.

The inflatable cuff 15, the pressure sensor 40, the pulse wave discrimination circuit 54, the static pressure discrimination circuit 52 and the A/D converters 56 and 60 cooperate with one another to provide a pulse wave sensor that detects a pressure pulse wave that propagates through an artery of the living subject.

The electronic control device 58 preferably includes a central processing unit (CPU) 62, a read-only memory (ROM) 64, a random access memory (RAM) 66 and an input-output (I/O) port. The CPU 62 processes input signals according to control programs pre-stored in the ROM 64 using the RAM 66 as temporary storage. In addition, the CPU 62 outputs a drive signal to the printer 26, and outputs display signals to the displays 32, 34, 36 and 38.

When a blood pressure measurement is initiated, CPU 62 supplies a drive signal to the DC motor 48. The DC motor 48 winds the belt 16 to tighten the inflatable cuff 15 around the subject's right arm 12.

Next, the CPU 62 supplies a control signal to the switch valve 42 to place it in the inflation position and then supplies a drive signal to the air pump 44 to inflate the inflatable cuff 15, thereby compressing the upper portion of the subject's right arm 12. The CPU 62 then supplies a control signal to the switch valve 42 to place it in the slow-deflation position. This allows the air pressure in the inflatable cuff 15 to gradually decrease.

While the air pressure in the inflatable cuff 15 gradually decreases, the CPU 62 obtains the pulse wave signal $SM_1$ and the cuff pressure signal SK from the pressure sensor 40 via the pulse wave discrimination circuit 54 and the static pressure discrimination circuit 52, respectively. The CPU 62 determines the subject's systolic blood pressure value SBP, the subject's diastolic blood pressure value DBP and the subject's mean blood pressure value MBP based on the obtained signals $SM_1$ and SK using well-known oscillimetric blood pressure measuring techniques. In addition, the CPU 62 determines the subject's heart rate based on the time gap between successive pulses of the pressure pulse wave.

The CPU 62 then supplies display signals to the systolic blood pressure display 32 and the diastolic blood pressure display 34 to display the determined blood pressure values SBP and DBP, respectively. In addition, the CPU 62 produces a set of blood pressure data that represents the determined blood pressure values SBP, DBP and MBP, the determined heart rate, and a date and a time when the values were determined. The CPU 62 stores the set of blood pressure data in a blood pressure data storing area of a memory device 68. The memory device 68 preferably stores a plurality of sets of blood pressure data produced during a plurality of blood pressure measuring operations.

The memory device 68 may be implemented by any known data storing device, such as a magnetic disk, a magnetic tape, static or dynamic RAM, a floppy disk and disk drive, a writable optical disk and disk drive, a hard drive, flash memory or the like.

The automatic blood pressure measuring device 8 includes an electrocardiographic waveform determiner 70. The electrocardiographic waveform determiner 70 continuously detects an electrocardiographic waveform that indicates the change in electric potential of the subject's cardiac muscle. The electrocardiographic waveform determiner 70 determines the electrocardiographic waveform from signals supplied by the electrocardio electrodes 18a and 18b. The electrocardiographic waveform determiner 70 supplies the electrocardiographic waveform to the electronic control device 58 as an electrocardio signal $SM_2$.

Figure 3:
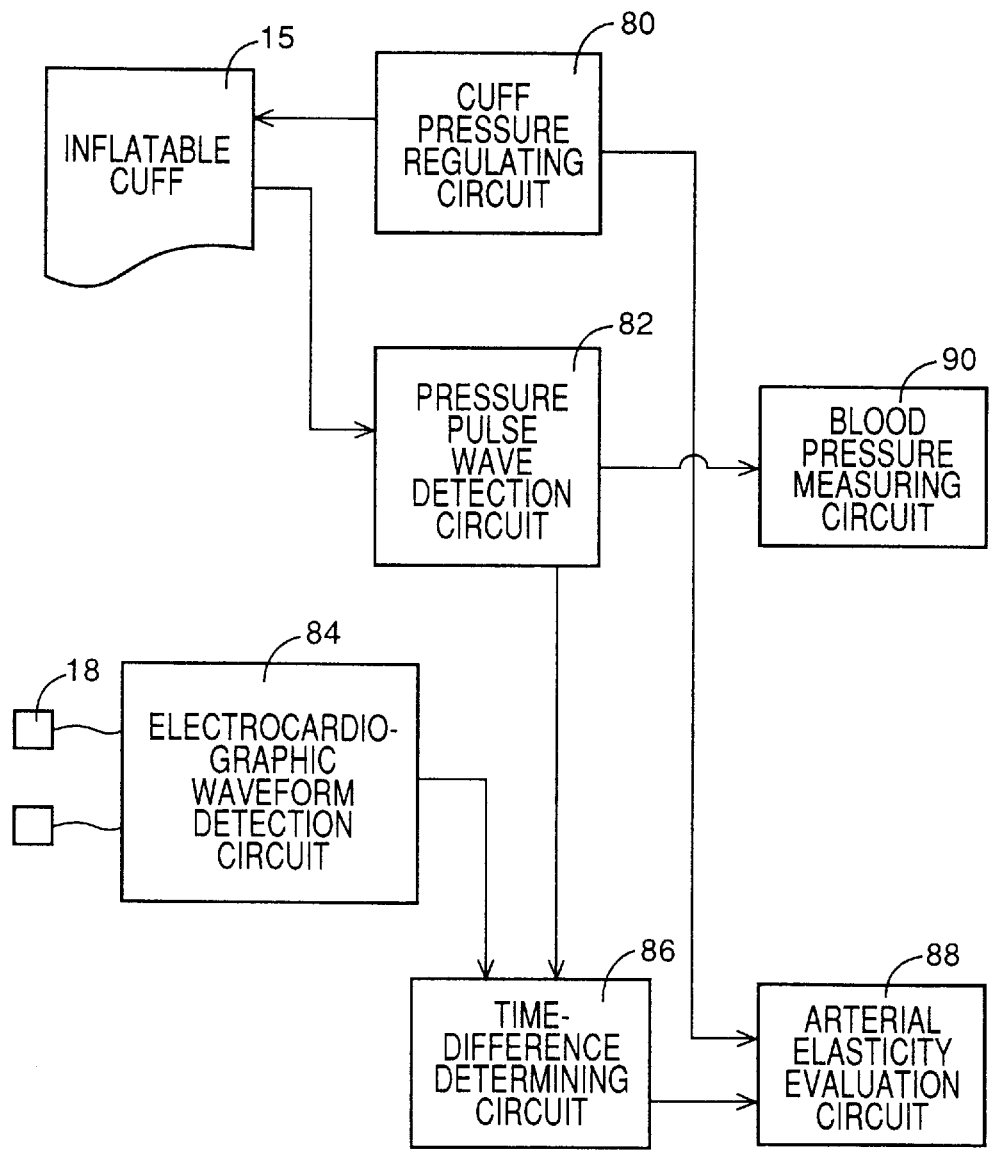
FIG. 3 is a block diagram of an electronic control device of the automatic blood pressure measurement device of FIG. 1.

FIG. 3 illustrates the control functions of the electronic control device 58 of the automatic blood pressure measuring device 8.

The electronic control device 58 regulates the air pressure in the inflatable cuff 15 via a cuff pressure regulating circuit 80. When a blood pressure measurement is initiated, the cuff pressure regulating circuit 80 switches the switch valve 42 to the inflation position and drives the air pump 44 to quickly increase the air pressure in the inflatable cuff 15 to a predetermined target value $P_1$, e.g., 180 mmHg. Subsequently, the cuff pressure regulating circuit 80 switches the switch valve 42 to the slow-deflation position to slowly decrease the air pressure in the inflatable cuff 15.

While the air pressure in the inflatable cuff 15 gradually decreases, a blood pressure measuring circuit 90 uses well-known oscillimetric techniques to measure the subject's systolic blood pressure, the subject's diastolic blood pressure and the subject's mean blood pressure. The blood pressure measurement is based on the variation of the amplitudes of the heartbeat-synchronous pulses of the pressure pulse wave detected by a pressure pulse wave detection circuit 82 while the air pressure in the inflatable cuff 15 is gradually decreased. The electronic control device 58 also measures the subject's heart rate based on the time gap between successive pulses of the pressure pulse wave.

Figure 4:
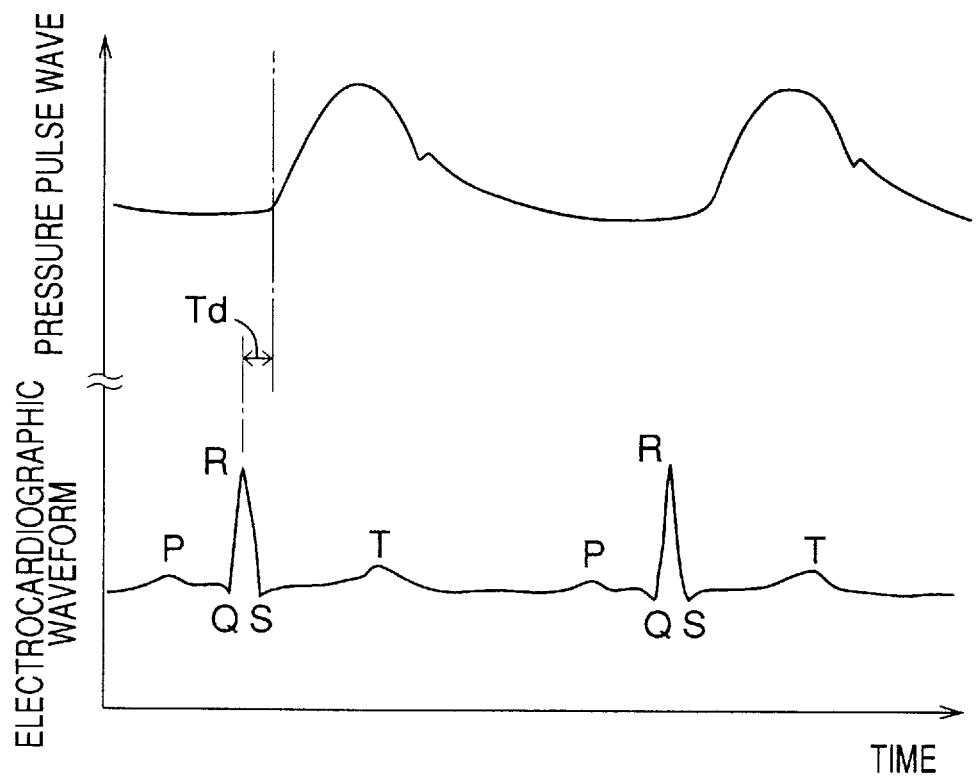
FIG. 4 is a timing chart of the electronic control device of the automatic blood pressure measurement device of FIG. 1.

In addition, a time-difference determining circuit 86 determines a time difference Td between a predetermined periodic point on the electrocardiographic waveform and a predetermined periodic point on the pressure pulse wave. In the preferred embodiment, the time-difference determining circuit 86 determines the time difference Td between an R point on the electrocardiographic waveform and a rise point of the pressure pulse wave, as shown in FIG. 4.

An arterial elasticity evaluation circuit 88 evaluates a degree of elasticity of the subject's arteries based on changes in the time difference Td determined by the time-difference determining circuit 86 while the constriction pressure applied by the inflatable cuff 15 is changed by the cuff pressure regulating circuit 80.

Figure 5:
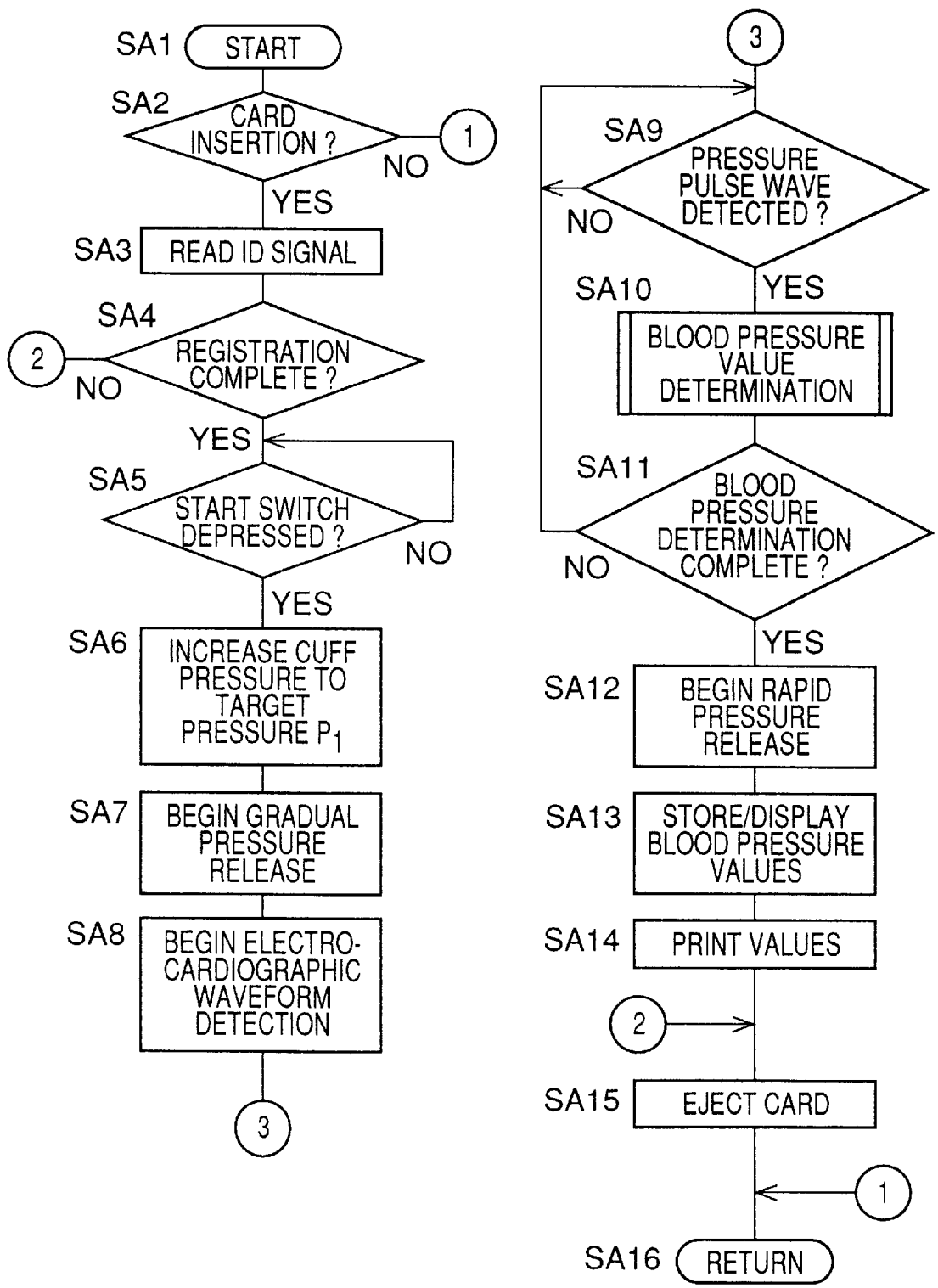
FIGS. 5 is a flowchart of a preferred control routine for the automatic blood pressure measurement device of FIG. 1.
Figure 6:
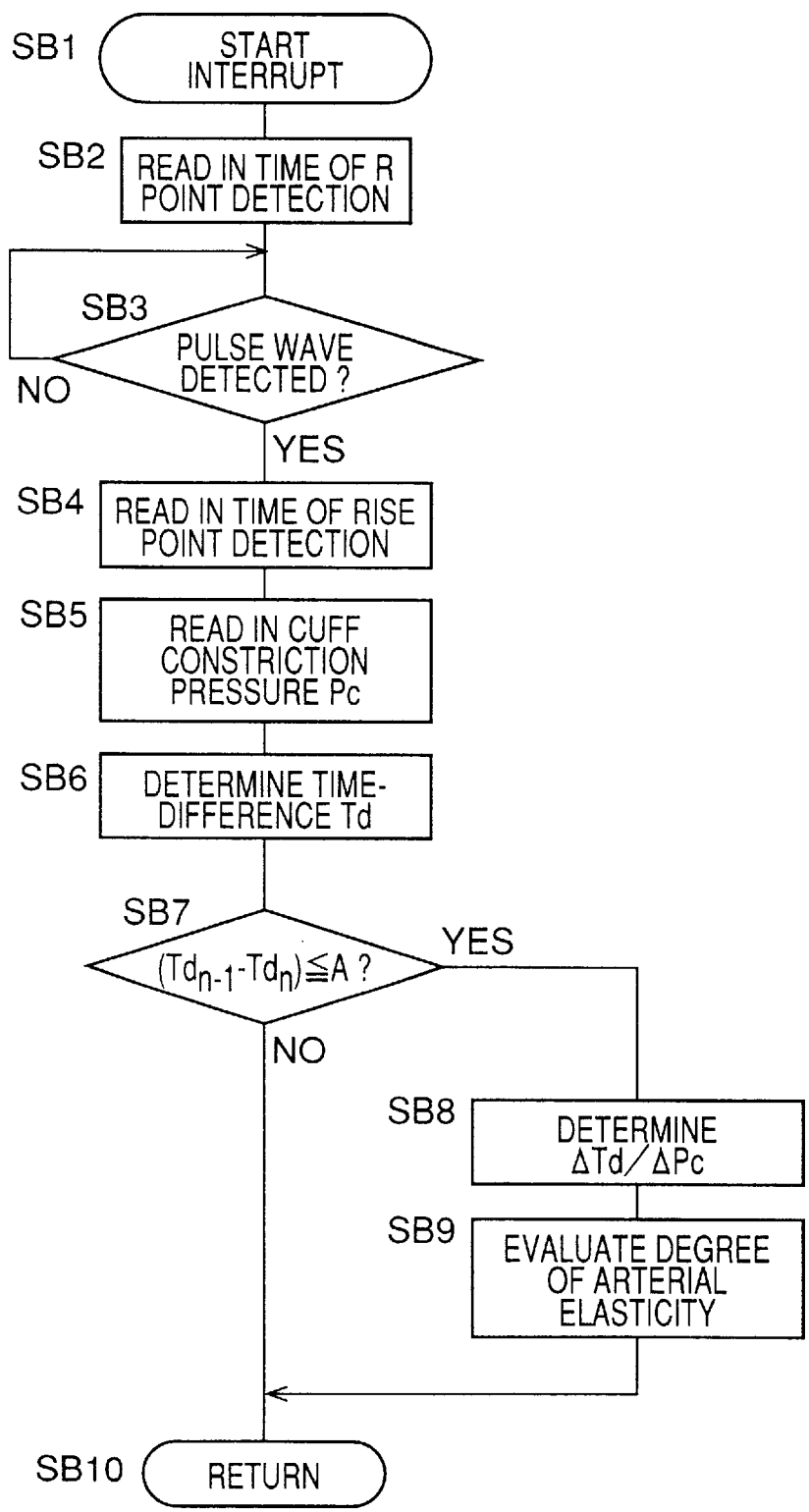
FIG. 6 is a flowchart of a preferred interrupt routine for the automatic blood pressure measurement device of FIG. 1.

FIG. 5 outlines a preferred control routine for determining the blood pressure and heart rate of the subject. FIG. 6 outlines a preferred interrupt routine for the arterial elasticity evaluation system of this invention.

As shown in FIG. 5, the routine starts at step SA1 and proceeds to step SA2, where the control system determines if a magnetic card 74 has been inserted into the card insertion opening 28 of the card reader 72. If a card has been inserted, control continues to step SA3. Otherwise, control jumps to step SA16, where the control routine stops.

In step SA3, the control system reads an ID signal recorded on the magnetic card 74. Control then continues to step SA4, where the control system determines if the ID signal corresponds to a pre-registered signal stored in the memory device 68. If the ID signal corresponds to a pre-registered signal, control continues to step SA5. Otherwise, control jumps to step SA15. In step SA15, the magnetic card 74 is ejected from the card reader 72. Control then continues from step SA15 to step SA16.

In step SA5, the control system determines if the start switch 22 has been depressed. If the start switch 22 is depressed, control continues to step SA6. Otherwise, control jumps back to step SA5.

In step SA6, the control system increases the air pressure in the inflatable cuff 15 until the target cuff pressure value $P_1$ is reached. The control system accomplishes this by driving the drum 50 to tighten the belt 16 and the inflatable cuff 15 around the subject's right arm 12. At the same time, the control system switches the switch valve 42 to the inflation position and turns on the air pump 44. When the air pressure in the inflatable cuff 15 reaches the predetermined pressure $P_1$, the control system stops the air pump 44.

Next, in step SA7, the control system switches the switch valve 42 to the slow-deflation position. Accordingly, the air pressure in the inflatable cuff 15 gradually decreases. Control then continues to step SA8, where the control system begins detecting the subject's electrocardiographic waveform.

Then, in step SA9, the control system determines if the pressure pulse wave signal $SM_1$ has been detected. If the pressure pulse wave signal $SM_1$ is detected, control continues to step SA10. Otherwise, control jumps back to step SA9.

In step SA10, the control system determines the subject's systolic blood pressure, the subject's diastolic blood pressure and the subject's mean blood pressure from the changes in the amplitudes in the pressure pulse waves detected during the gradual release of air from the inflatable cuff 15. As discussed above, the subject's blood pressure is determined using well-known oscillimetric techniques. In addition, the control system determines the subject's heart rate based on the time gap between successive pulses of the pressure pulse wave. Control then continues to step SA12, where the control system switches the switch valve 42 to the quick-deflation position to rapidly decrease the air pressure in the inflatable cuff 15.

Next, at step SA13, the control system stores the determined systolic blood pressure, the determined diastolic blood pressure, the determined mean blood pressure, the determined heart rate, and the time and date of the measurement in the memory device 68. In addition, the control system displays the systolic blood pressure value on the display 32, the diastolic blood pressure value on the display 34, and the heart rate on the display 36.

Then, at step SA14, the control system prints out the determined values in a preferred format described in more detail below. Control then continues to step SA15.

At any time during the measurement process, when the electrocardiographic waveform detection circuit 84 detects an R point of the electrocardiographic waveform, the control system interrupts the control routine outlined in FIG. 5 and initiates the control routine outlined in FIG. 6.

As shown in FIG. 6, the interrupt routine starts at step SB1 and proceeds to step SB2, where the control system reads in the time at which the R point of the electrocardiograph waveform was detected.

Next, in step SB3, the control system determines if the pressure pulse wave has been detected by the pressure pulse wave detection circuit 82. If the pressure pulse wave has been detected, control continues to step SB4. Otherwise, control jumps back to step SB3.

In step SB4, the control system reads in the time at which the rise point of pressure pulse wave was detected. Control then continues to step SB5, where the control system reads in the cuff constriction pressure $P_c$ detected by the pressure sensor 40. Next, at step SB6, the time-difference determining circuit 86 determines the time difference Td between the R point of the electrocardiographic waveform and the rise point of the pressure pulse wave.

Then, at step SB7, the control system determines if the time difference determined for the previous cycle $Td_{n-1}$ minus the time difference determined for the present cycle $Td_n$ is less than or equal to a predetermined value A. If $(Td_{n-1}-Td_n)$ is not less than or equal to A, control jumps to step SB10. Otherwise, control continues to step SB8. The predetermined value A is experimentally determined in advance. When $(Td_{n-1}-Td_n)$ is less than or equal to A, the time difference Td no longer changes by a significant amount as the constriction pressure $P_c$ changes.

Figure 7:
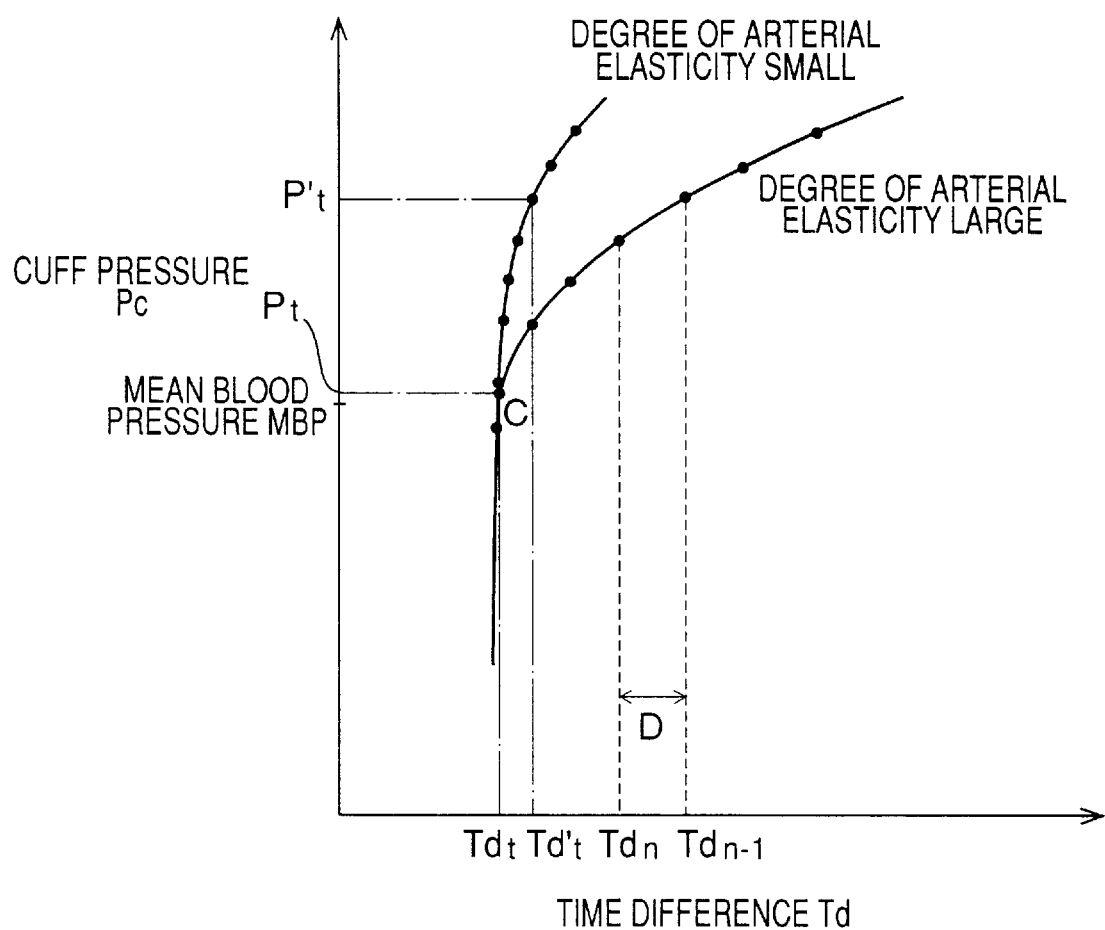
FIG. 7 shows a relationship between a constriction pressure applied by the inflatable cuff and a corresponding time difference determined by the time-difference determining circuit for different degrees of arterial elasticity.

In step SB8, the control system plots the relationship between the time difference Td determined at step SB6 and the cuff constriction pressure $P_c$ determined at step SB5. As shown in FIG. 7, the resulting graph is preferably a two-dimensional curve, with the time difference Td plotted along one axis and the cuff constriction pressure $P_c$ plotted along an orthogonal axis. The control system then determines the slope $\Delta Td/\Delta Pc$ using the formula:

$$\Delta Td/\Delta Pc = (Td_t' - Td_t)/(P_t' - P_t) \qquad (1)$$

where:

$P_t$ is a cuff pressure at which the time difference Td begins to change as the cuff pressure changes (indicated by the inflection point C in the curve shown in FIG. 7);

$P_t'$ is a cuff constriction pressure greater than the cuff pressure $P_t$ by a predetermined value (e.g., 50 mmHg);

$Td_t'$ is a time difference corresponding to the cuff constriction pressure $P_t'$; and $Td_t$ is a time difference corresponding to the cuff constriction pressure $P_t$.

Figure 8:
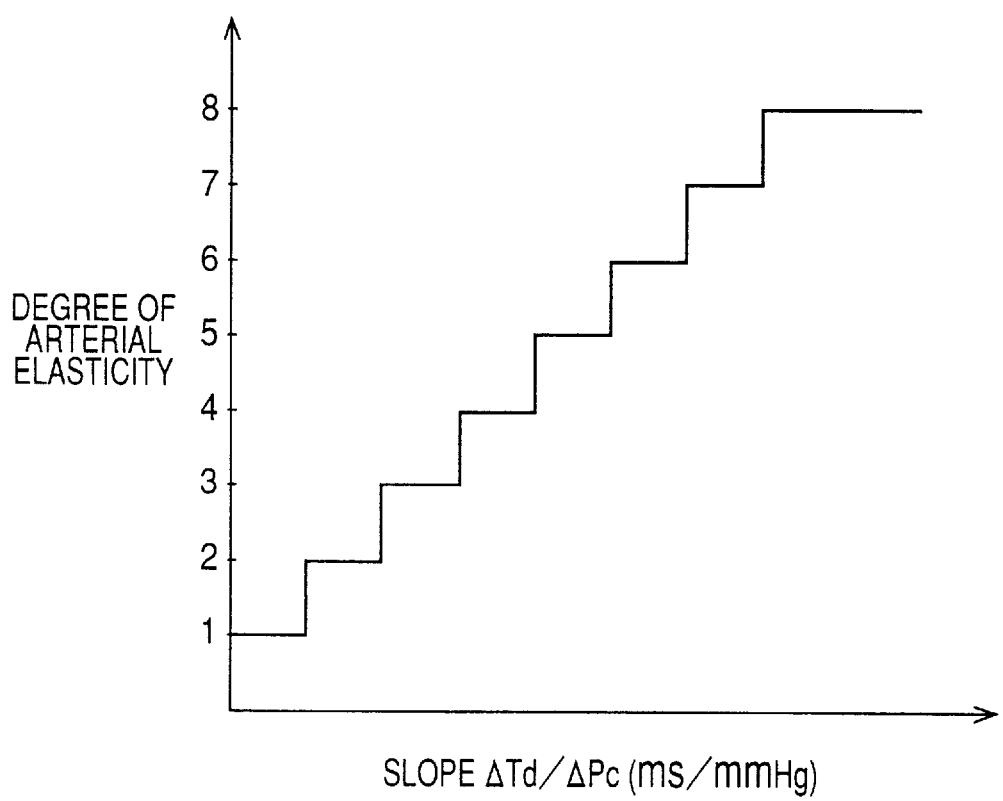
FIG. 8 is a graph relating the degree of arterial elasticity in a subject to the slope $\Delta Td/\Delta Pc$.

Next, at step SB9, the control system evaluates the degree of arterial elasticity based on the slope determined at step SB8. In the preferred embodiment, the control system determines a degree of arterial elasticity using a look-up table, such as a table representing the graph shown in FIG. 8. As shown by the graph of FIG. 8, as the slope ΔTd/ΔPc increases, the degree of arterial elasticity increases. Control then continues to step SB10, where the control system returns to the control routine of FIG. 5.

Figure 9:
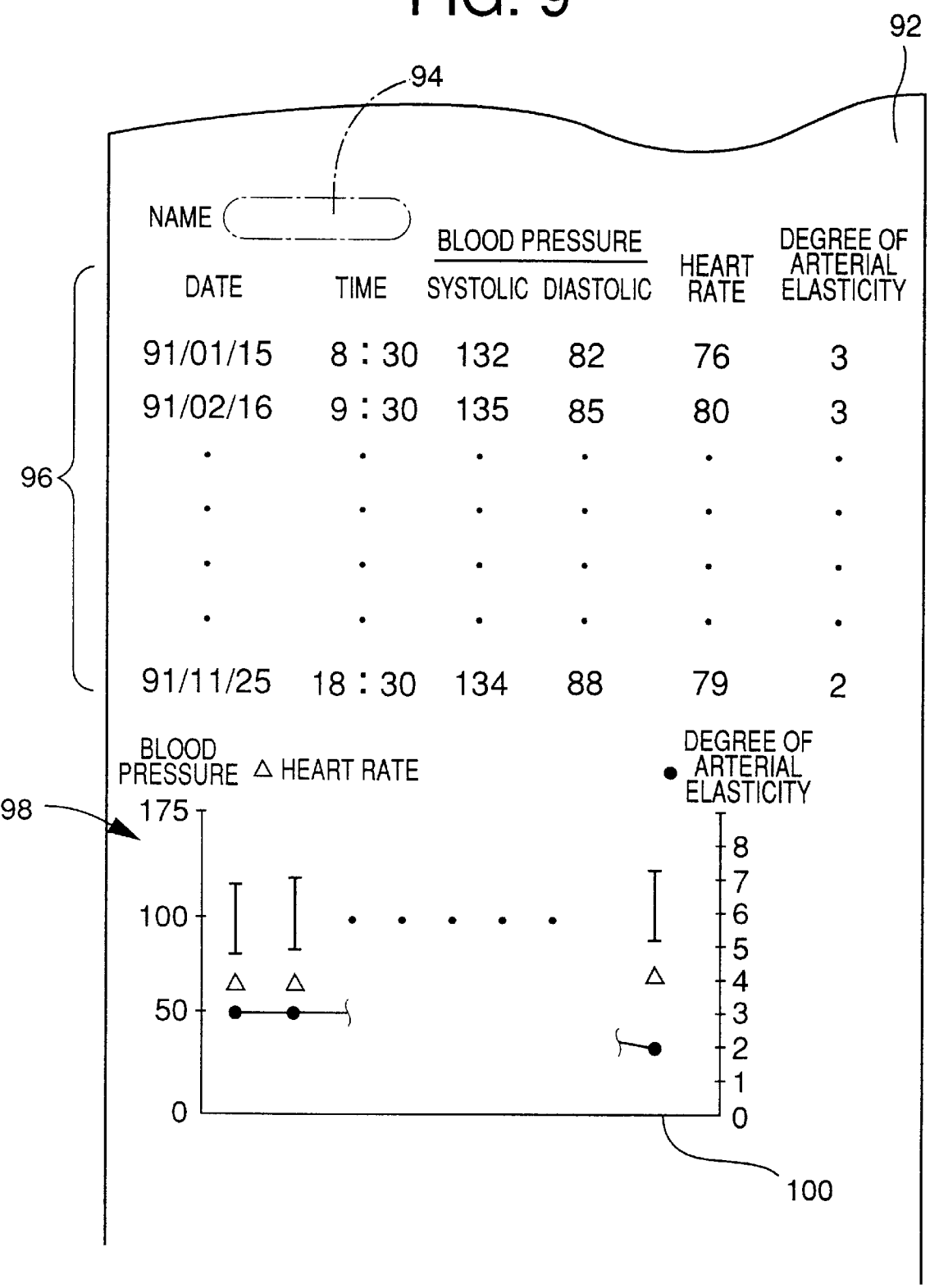
FIG. 9 shows a printout output from a printer of the automatic blood pressure measurement device of FIG. 1.

The values printed by the control system at step SA14 are preferably printed by the printer 26 using the format shown in FIG. 9. The printout 92 preferably includes the name 94 of the subject measured, the date of the measurements, the times of measurement, the systolic blood pressure values, the diastolic blood pressure values, the heart rates, and the degrees of arterial elasticity.

In the preferred embodiment, the control system stores a set of measurements performed at different times for each subject, and displays the full set of measurements 96 on the printout 92.

In addition, the printout 92 preferably includes a trend graph 98. In the trend graph 98, the "I"-shaped points indicate the systolic and the diastolic blood pressure. The blood pressure values are read along the left vertical axis of the trend graph 98, with the upper end of the "I" indicating the systolic blood pressure and the lower end of the "I" indicating the diastolic blood pressure. In addition, the "Δ" symbol indicates the heart rate, which is read along the left vertical axis, and the black circles indicate the degree of arterial elasticity, which is read along the right vertical axis. The horizontal axis 100 represents the date of measurement.

The electronic control device 58, including the cuff pressure regulating circuit 80, the pressure pulse wave detection circuit 82, the blood pressure measuring circuit 90, the electrocardiographic waveform detection circuit 84, the time-difference determining circuit 86 and the arterial elasticity evaluation circuit 88, is preferably implemented using a programmed general purpose computer. However, the electronic control device 58 can also be implemented using a special purpose computer, a programmed microprocessor or microcontroller and peripheral integrated circuit element, an ASIC or other integrated circuit, a hardwired electronic or logic circuit such as a discrete element circuit, a programmable logic device such as a FPGA, a PLD, a PLA or a PAL, or the like. In general, any device on which a finite state machine capable of implementing the flowcharts shown in FIGS. 5 and 6 and capable of controlling the peripheral devices shown in FIGS. 2 and 3 can be used to implement the electronic control device 58 of this invention.

While this invention has been described in conjunction with the specific embodiment outlined above, it is evident that many alternatives, modifications and variations will be apparent to those skilled in the art. For example, although the arterial elasticity evaluation circuit 88 utilizes the time difference Td between an R point of the electrocardiographic waveform and a rise point of the oscillatory pressure pulse wave, it may also utilize a time difference between a Q point or an S point of the electrocardiographic waveform and a rise point of the oscillatory pressure pulse wave. In addition, the time difference may be defined from an R point, an S point or a Q point of the electrocardiographic waveform to a maximum point of the oscillatory pressure pulse wave. In general, the time difference may be defined from any predetermined periodic point in the electrocardiographic waveform to any predetermined periodic point on the pressure pulse wave.

In addition, although the arm receptor 14 in the automatic blood pressure measuring device 8 is adapted to receive the subject's right arm 12, it is possible to modify the automatic blood pressure measuring device 8 to receive the subject's left arm 13 through the arm receptor 14. In this configuration, the arm receptor 14 and the first arm rest 17 are provided on the left half portion of the housing 10, and the second arm rest 19 is provided on the right hand side of the housing 10.

Furthermore, although the first arm rest 17 is provided at a tilt, the arm rest 17 may also be formed to extend in a horizontal direction. In addition, the second arm rest 19 may be provided at a tilt. In either case, the arm rests 17 and 19 are required to support the subject's arms 12 and 13 so that the muscles of the arms 12 and 13 are kept in a relaxed state.

Although the electrocardio electrode 18a is provided on the free end portion of the first arm rest 17 and the electrocardio electrode 18b is provided on the end portion of the second arm rest 19, it is possible to position the electrocardio electrodes 18a and 18b at different positions on the arm rests 17 and 19. The positions of the electrocardio electrodes 18a and 18b will depend upon the shapes and positions of the arm rests 17 and 19.

Also, although the electrocardio electrodes 18a and 18b are attached to the arm rests 17 and 19, other electrocardio electrodes that are not attached to any part of the housing 10 may be used, either in addition to or in place of the electrocardio electrodes 18a and 18b.

In addition, although the inflatable cuff 15 in the automatic blood pressure measuring device 8 automatically wraps around the arm 12 of the subject during a mesurement, a manually-wrapped inflatable cuff may also be used.

Accordingly, the preferred embodiments of the invention as set forth above are intended to be illustrative, not limiting. Various changes may be made without departing from the spirit and scope of the invention as defined in the following claims.

What is claimed is:

1. A system for evaluating an arterial elasticity of a living subject, comprising:

a constriction device that applies a changing constriction pressure to a portion of the living subject;

a pressure pulse wave detection circuit that detects pressure pulse waves produced by a cardiac muscle of the living subject, the pressure pulse waves propagating through an artery of the living subject; and an arterial elasticity evaluation device that determines a degree of elasticity of arteries of the living subject based on the detected pressure pulse waves and the constriction pressure applied by the constriction device to the portion of the living subject, the arterial elasticity evaluation device comprising:

an electrocardiographic waveform determiner that determines an electrocardiographic waveform of the living subject;

a time-difference determining circuit that determines time differences between predetermined periodic points on the electrocardiographic waveform of the living subject and predetermined periodic points on corresponding pressure pulse waves of the living subject; and an arterial elasticity evaluation circuit that determines a degree of elasticity of arteries of the living subject based on a relationship between the time differences determined by the time-difference determining circuit and the constriction pressure applied by the constriction device to the portion of the living subject.

2. The system of claim 1, wherein the electrocardiographic waveform determiner comprises:

a plurality of electrocardio electrodes capable of sensing an electrocardiographic signal of the living subject when the electrocardio electrodes are in electrical contact with the living subject; and an electrocardiographic waveform detection circuit that detects the living subject's electrocardiographic waveform based on the electrocardiographic signals sensed by the electrocardio electrodes.

3. The system of claim 1, wherein the arterial elasticity evaluation circuit comprises means for determining a degree of elasticity of arteries of the living subject based on a relationship between changes in the time differences determined by the time-difference determining circuit and changes in the constriction pressure applied by the constriction device to the portion of the living subject.

4. The system of claim 1, wherein the time-difference determining circuit comprises means for determining time differences between R points on the electrocardiographic waveform and rise points on corresponding pressure pulse waves.

5. The system of claim 1, wherein the constriction device comprises:
   a cuff wrapable around a portion of the living subject that applies a constriction pressure to the portion of the living subject when the cuff is wrapped around the portion of the living subject; and
   a cuff pressure regulating circuit that controls the constriction pressure applied by the cuff to the portion of the living subject, the cuff pressure regulating circuit changing the constriction pressure applied by the cuff to the portion of the living subject during a measurement process.

6. The system of claim 1, further comprising a blood pressure measuring circuit that determines a blood pressure of the living subject.

7. The system of claim 6, wherein the blood pressure measuring circuit comprises means for determining a systolic blood pressure, a diastolic blood pressure, a mean blood pressure and a heart rate of the living subject.

8. An automatic blood pressure measurement system for measuring a blood pressure of a living subject, measuring an electrocardiographic waveform of the living subject, and evaluating an arterial elasticity of a living subject, comprising:
   a frame;
   a first arm rest attached to the frame and capable of supporting a right arm of the living subject;
   a first electrocardio electrode attached to the first arm rest and positioned to physically contact an arm of the living subject when the living subject's arm is resting on the first arm rest, the first electrode capable of detecting an electrocardiographic signal from the living subject when the living subject is in physical contact with the first electrocardio electrode;
   a second arm rest attached to the frame and capable of supporting a left arm of the living subject;
   a second electrocardio electrode attached to the second arm rest and positioned to physically contact an arm of the living subject when the living subject's arm is resting on the second arm rest, the second electrode capable of detecting an electrocardiographic signal from the living subject when the living subject is in physical contact with the second electrocardio electrode;
   a constriction device that applies a changing constriction pressure to a portion of the living subject;
   a pressure pulse wave detection circuit that detects pressure pulse waves produced by a cardiac muscle of the living subject, the pressure pulse waves propagating through an artery of the living subject;
   a blood pressure measuring circuit that determines a blood pressure of the living subject based on the detected pressure pulse waves; and
   an arterial elasticity evaluation device that determines a degree of elasticity of arteries of the living subject based on the detected pressure pulse waves and the constriction pressure applied by the constriction device to the portion of the living subject.

9. The system of claim 8, wherein the arterial elasticity evaluation device comprises:
   an electrocardiographic waveform determiner that determines an electrocardiographic waveform of the living subject;
   a time-difference determining circuit that determines time differences between predetermined periodic points on the electrocardiographic waveform of the living subject and predetermined periodic points on corresponding pressure pulse waves of the living subject; and
   an arterial elasticity evaluation circuit that determines a degree of elasticity of arteries of the living subject based on a relationship between the time differences determined by the time-difference determining circuit and the constriction pressure applied by the cuff to the portion of the living subject.

10. The system of claim 9, wherein the electrocardiographic waveform determiner comprises:
    the first and second electrocardio electrodes; and
    an electrocardiographic waveform detection circuit that detects the living subject's electrocardiographic waveform based on the electrocardiographic signals sensed by the electrocardio electrodes.

11. The system of claim 9, wherein the arterial elasticity evaluation circuit comprises means for determining a degree of elasticity of arteries of the living subject based on a relationship between changes in the time differences determined by the time-difference determining circuit and changes in the constriction pressure applied by the cuff to the portion of the living subject.

12. The system of claim 9, wherein the time-difference determining circuit comprises means for determining time differences between R points on the electrocardiographic waveform and rise points on corresponding pressure pulse waves.

13. The automatic blood pressure measurement system of claim 8, wherein the constriction device comprises:
    an arm receptor positioned on the frame to receive an arm of the living subject;
    an inflatable cuff positioned inside the arm receptor capable of compressing an arm of the living subject; and
    an air pump connected to the inflatable cuff.

14. The automatic blood pressure measurement system of claim 8, wherein the blood pressure measuring circuit comprises means for determining a systolic blood pressure, a diastolic blood pressure, a mean blood pressure and a heart rate of the living subject.

15. A system for evaluating an arterial elasticity of a living subject, comprising:
    a constriction device that applies a changing constriction pressure to a first portion of the living subject;
    a first pulse wave detection circuit that detects first pulse waves from the first portion of the living subject;
    a second pulse wave detection circuit that detects corresponding second pulse waves from a second portion of the living subject;

a time-difference determining circuit that determines time differences between predetermined periodic points on the first pulse waves and predetermined periodic points on the corresponding second pulse waves; and an arterial elasticity evaluation device that determines a degree of elasticity of arteries of the living subject based on a relationship between changes in the constriction pressure applied by the constriction device to the first portion of the living subject and changes in the time differences determined by the time-difference determining circuit.

16. The system of claim 15, wherein the arterial elasticity evaluation device comprises:

rate-of-change determining means for determining a rate of change of the time differences determined by the time-difference determining circuit with respect to the constriction pressure applied by the constriction device to the first portion of the subject; and means for determining a degree of elasticity of the subject based on the rate of change determined by the rate-of-change determining means.

17. The system of claim 15, further comprising:

a memory that stores a plurality of values each of which is determined as the degree of elasticity of arteries of the subject by the arterial elasticity evaluation device in a corresponding one of a plurality of measuring operations; and an output device which outputs, along a time axis, a trend graph including the values stored in the memory.

18. A method of evaluating an arterial elasticity of a living subject, comprising:

applying a changing constriction pressure to a portion of the living subject;

measuring pressure pulse waves produced by a cardiac muscle of the living subject;

determining a degree of elasticity of a living subject's arteries based on the detected pressure pulse waves and the changing constriction pressure; and measuring a blood pressure of the living subject based on the detected pressure pulse waves.

19. The method of claim 18, wherein determining a degree of elasticity of the living subject's arteries comprises:

measuring an electrocardiographic waveform of the living subject;

determining time differences between predetermined periodic points on the electrocardiographic waveform of the living subject and predetermined periodic points on corresponding pressure pulse waves of the living subject; and determining a degree of arterial elasticity of a living subject's arteries based on a relationship between the determined time differences and the constriction pressure applied to the portion of the living subject.

20. The method of claim 19, wherein determining a degree of elasticity of a living subject's arteries comprises determining a degree of elasticity of a living subject's arteries based on a relationship between changes in the determined time differences and changes in the constriction pressure applied to the portion of the living subject.

21. The method of claim 18, wherein applying a changing constriction pressure to the portion of the living subject comprises:

wrapping an inflatable cuff around an arm of the living subject; and changing an air pressure in the inflatable cuff.

22. The method of claim 18, wherein measuring a blood pressure of the living subject based on the detected pressure pulse waves comprises measuring a systolic blood pressure, a diastolic blood pressure, a mean blood pressure, and a heart rate of the living subject based on the detected pressure pulse waves.

* * * * *